United States Patent [19]
Shibutani et al.

[11] Patent Number: 5,652,231
[45] Date of Patent: Jul. 29, 1997

[54] CARCINOSTATIC FOR HORMONOTHERAPY CONTAINING DIENOGEST AS EFFECTIVE COMPONENT

[75] Inventors: Yasunori Shibutani; Masaomi Obata; Masami Sato; Yukio Katsuki, all of Tokyo, Japan

[73] Assignee: Mochida Pharmaceutical Co., Ltd., Tokyo, Japan

[21] Appl. No.: 341,927

[22] Filed: Nov. 16, 1994

[30] Foreign Application Priority Data

Nov. 19, 1993 [JP] Japan ................................. 5-290823

[51] Int. Cl.⁶ ........................................ A61K 31/56
[52] U.S. Cl. ................................................ 514/179
[58] Field of Search ................................. 514/179

[56] References Cited

FOREIGN PATENT DOCUMENTS

| | | |
|---|---|---|
| 63-72627 | 4/1988 | Japan . |
| 64-3121 | 1/1989 | Japan . |
| 64-3122 | 1/1989 | Japan . |
| 1524917 | 9/1978 | United Kingdom . |
| WO9100732 | 1/1991 | WIPO . |

OTHER PUBLICATIONS

Nikschick et al., Exp. Clin. Endocrinol, (Sep. 1989) vol. 94 (1–2) pp. 211–214.

"Endometriosetherapie Mit Dienogest" by G. Kohler et al., Zent. BL. Gynakol, vol. 109, No. 12, 1987, pp. 795–801. Abstract only.

Ishizaki et al. Acta Obst. Gynec Jpn., vol. 44, No. 1, pp. 67–72 (1992) Abstract only.

Morisawa et al., J. Jpn. Soc. Clin. Cytol., vol. 26, No. 3, pp. 433–442 (May 1987). Summary only.

"Synthesis, Effects, and Metabolism of the Progestagen and Potential Interceptive Dienogest" by K. Schubert et al. Natural Products Chemistry, 1984, pp. 143–158.

"Martindale, The Extra Pharmacopoeia" edited by J.E.F. Reynolds, The Pharmaceutical Press, 1989, pp. 1386–1387.

"Progestational Agents in the Treatment of Breast Cancer", Cancer Treat Res., vol. 39, 1988, pp. 147–157.

"Lipid Metabolism During Treatment of Endometriosis with the Progestin Dienogest" by G. Kohler et al, Acta Obstetricia et Gynecologica Scandinavica, vol. 68, No. 7, 1989, pp. 633–635.

*Primary Examiner*—Jerome Goldberg
*Attorney, Agent, or Firm*—Birch, Stewart, Kolasch & Birch, LLP

[57] ABSTRACT

A carcinostatic for a hormonotherapy containing dienogest or its solvate, which is expected to exert therapeutic effects for a broad range of cancer cases at a far lower dose than that of conventional hormonotherapeutic agents and utterly free from side effects that the conventional high-dose hormonotherapy had suffered.

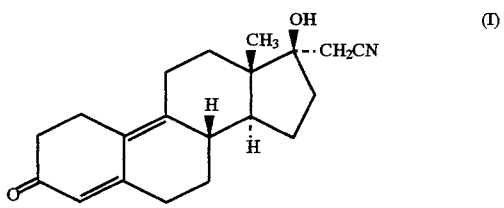

24 Claims, No Drawings

CARCINOSTATIC FOR HORMONOTHERAPY CONTAINING DIENOGEST AS EFFECTIVE COMPONENT

BACKGROUND OF THE INVENTION

1. Field of the Invention

This invention relates to a carcinostatic for a hormonotherapy containing dienogest or its solvate as an effective component, a therapeutic agent for a sex hormone-dependent cancer containing dienogest or its solvate as an effective component, or a therapeutic agent for uterine cancer and/or breast cancer, which contains dienogest or its solvate as an effective component.

2. The State of the Art

Dienogest is the International Nonproprietary Names (INN) of a known compound, (17α-cyanomethyl-17β-hydroxyestra-4,9(10)-dien-3-one) having a structure represented by formula (I):

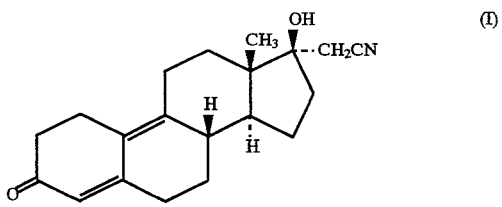

The nature and synthesis of this compound are compactly described in Schubert et al., Elsevier Science Publishers ed., Natural Products Chemistry, 1984, 143–158.

Dienogest is known to have progestational activity, and in Germany, a combined drug of dienogest with ethynylestradiol is recently purchased as an oral contraceptive. Use of the dienogest as a therapeutic agent for endometriosis has also been attempted (Exp. Clin. Endocrinol. 94, 1–2, 211, 1989). However, there has so far been no report indicating the carcinostatic activity of the dienogest.

It has also been reported that dienogest is free from androgenic activity, which is different from other compounds with progestational activity (Schubert et al., Elsevier Science Publishers ed., Natural Products Chemistry, 1984, 143–158, supra).

One current research theme in the field of cancer and hormone is "hormone dependency of cancer", and various researches are made on the influence of biological hormones on the initiation, promotion and progression of cancer. In view of such researches, hormonotherapy has become an important pharmacotherapy in treating typical sex hormone-dependent cancers such as uterine (endometrial carcinoma) cancer, breast cancer, prostate cancer, and thyroid gland cancer.

For example, more than 95% of uterine cancer are adenocarcinoma, and the cells in the uterine cancer lesion often retain some of the characteristics of epitherial cells of the endometrium in its proliferative phase. Such cells are believed to proliferate in the absence of progesterone by the stimulation of estrogen (Gurpide, J. Natl. Cancer Inst., 83, 6, 405–416, 1991). In view of such reports, hormonotherapies utilizing antiestrogens or progestins have been attempted as a pharmacotherapy in addition to conventional chemotherapies for the uterine cancer.

Antiestrogens such as tamoxifen and its derivatives have been attempted for use in such hormonotherapy. With regard to such antiestrogens, it has been reported that tamoxifen or its derivatives rather promoted the growth of uterine cancer cell lines, and that a long-term administration of tamoxifen as an adjuvant to which chemotherapy of breast cancer resulted in an increased risk of the uterine cancer incidence. Moreover, sensitivity of the uterine cancer cells to antiestrogens is not uniform, so that therapeutic effectivity of the use of an antiestrogen for the uterine cancer is not yet confirmed. (Gurpide, J. Natl. Cancer Inst., 83, 6, 405–416, 1991, supra.)

With regard to the progestins, use of orally administrable 17α-hydroxyprogesterone, megestrol, medrogestone, and medroxyprogesterone in hormonotherapy has been attempted. Among these, medroxyprogesterone has been found to have therapeutic effects for the uterine cancer when it is administered at a high daily dose of from 400 to 600 mg (Kurihara et al., Sanfujinka-no Jissai (Obstetrical and Gynecological Practice), 34, 517–536, 1985), and a high dose preparation of medroxyprogesterone has been developed and purchased.

However, even when the medroxyprogesterone is administered at such a high dose, the percentage of successful therapy is still 23.6% (Kurihara et al., Sanfujinka-no Jissai (Obstetrical and Gynecological Practice), 34, 517–536, 1985, supra), while side effects of the medroxyprogesterone, which are believed to be caused by corticoid activity or androgenic activity of the medroxyprogesterone, become notable. Accordingly, the medroxyprogesterone can inevitably be used with caution (Okada et al., Sanfujinka-no Jissai (Obstetrical and Gynecological Practice), 38, 4, 575–582, 1989).

Almost all breast cancer and prostate cancer are believed to be caused under the actions of estrogen and androgen. Hormonotherapies using antiestrogens or progestins are also attempted in the treatment of the breast cancer as a pharmacotherapy, as in the case of the above-described uterine cancer. Typical antiestrogens are tamoxifen and its derivatives. However, these antiestrogens are not necessarily optimal since induce from side effects including blood disorders such as leukopenia and hypercalcemia as well as an increased risk of the uterine cancer incidence after a long-term administration as mentioned above. Typical progestin is the above-described medroxyprogesterone. However, as in the case of uterine cancer, medroxyprogesterone has to be administered at a high dose, i.e. at a daily dose of from 600 to 1,200 mg, and the above-mentioned side effects, which are believed to be caused by the corticoid activity or the androgenic activity of the medroxyprogesterone, become notable.

In the treatment of prostate cancer, therapies using the progestins has been attempted in addition to the therapies using estrogens.

Recently, cases have been reported wherein serious thrombosis in brain, heart, lung and the like have been induced as side effects of a high dose administration of medroxyprogesterone in treating sex hormone-dependent cancers, in particular, uterine cancer and breast cancer. In view of such situation, Safety Division of the Pharmaceutical Affairs Bureau, Japanese Ministry of Health and Welfare has called for an attention to the development of thrombosis in the use of medroxyprogesterone (Iyakuhin Kenkyu (Researches on Pharmaceuticals), 23, 5, 664–671, 1992).

As described above, the sufficient effective percentage of successful therapy in the hormonotherapy for sex hormone-dependent cancer is not still achieved, and such hormonotherapy is accompanied with serious side effects. In improving the therapeutic effects as well as the safety of such hormonotherapy in the sex hormone-dependent cancers, it is a matter of urgency to develop a drug that has a novel pharmacological activity and exhibits a broader range of therapeutic effects including the effects for the sex hormone-dependent cancers that had failed to respond to the conventional hormonotherapies. Such drug should also exert its therapeutic effects at a low dose, and has least side effects including thrombosis, cardiocoronary diseases, arteriosclerosis, Cushing's syndrome, and moon face, that are believed to be induced by the androgenic activity or the corticoid activity of the drug.

SUMMARY OF THE INVENTION

An object of the present invention is to provide a carcinostatic for a hormonotherapy containing, as its effective component, dienogest which is superior in the effectivity and weaker in the side effects compared to the conventional carcinostatics. Another object of the present invention is to provide a therapeutic agent for a sex hormone-dependent cancer containing dienogest or its solvate as an effective component, or to provide a therapeutic agent for uterine cancer and/or breast cancer which contains dienogest as its effective component.

DETAILED DESCRIPTION OF THE INVENTION

The inventors of the present invention have made an intensive study to develop a therapeutic agent which has a broad-range inhibitory effectivity for the sex hormone-dependent cancers including the uterine cancer and the breast cancer, and which is superior in the therapeutic effects and weaker in the side effects than the conventional carcinostatics. After such study, the inventors found that dienogest used at a significantly lower dose than the medroxyprogesterone or the tamoxifen is capable of inhibiting the growth of cell lines from the human sex hormone-dependent cancers to an extent significantly stronger than such conventional carcinostatics.

Dienogest also exhibited a significant inhibition of the growth of the cancer cell line whose growth was not at all inhibited by the medroxyprogesterone. It was also newly found that dienogest is free from the corticoid activity to enable its use as a therapeutic agent with less side effects. The present invention has been completed on such findings.

The present invention is directed to a pharmaceutical composition comprises dienogest or its solvate. In detail, the present invention is directed to a carcinostatic for a hormonotherapy, a therapeutic agent for sex hormone-dependent cancer or a therapeutic agent for uterine cancer and/or breast cancer, those of which comprise a pharmaceutically acceptable carrier and an effective amount of dienogest or its solvate.

The present invention is directed to a use of dienogest or a solvate thereof for the manufacture of a pharmaceutical composition for the treatment and/or prevention of cancer by hormonotherapy, of sex hormone-dependent cancer, or of uterine cancer and/or breast cancer.

The present invention is also directed to production process of carcinostatic for a hormonotherapy, preventive and/or therapeutic agent for sex hormone-dependent cancers, uterine cancer and/or breast cancer.

The present invention is further directed to a hormonotherapy of cancer, a method of treatment and/or prophylaxis of sex hormone-dependent cancer, uterine cancer and/or breast cancer.

Dienogest, which is the effective component in the carcinostatic of the present invention, is a compound having a structure represented by the following formula (I):

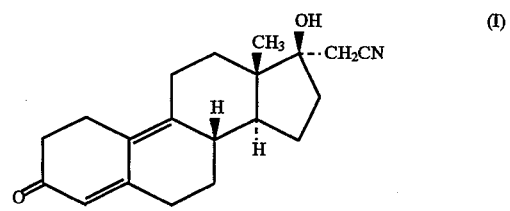

In the carcinostatic of the present invention, dienogest may be present as a solvate with any of various pharmaceutically acceptable solvents including water, ethanol, glycerol, and acetic acid.

Experiments

The Experiments as described below demonstrate the effects of the carcinostatic according to the present invention. Of the drugs used for comparison purpose, medroxyprogesterone is the only drug that is approved in Japan for the hormonotherapy of the uterine cancer and that can be orally applied as in the case of dienogest.

Experiment 1: Growth Inhibitory Action for a Cell Line from Human Well-Differentiated Uterine Cancer (Ishikawa Cell Line)

CB-17 SCID (severe combined immunodeficiency) female mice having a body weight of from 17 to 27 g, and Ishikawa cell line (Holinka et al., J. Steroid. Biochem., 24, 1, 85–89, 1986), which is a cell line from human well-differentiated uterine cancer, were used. The cell line culture was subcutaneously implanted in the back of one mouse. After confirming the capability of the cell line to grow to a cancer lesion at a volume of more than 1,000 mm$^3$, the cancer was extirpated and cut into pieces, which were subcutaneously implanted in the back of other 35 mice at 40 mg/mouse. When the implanted cancer had grown to a volume of 75 mm$^3$ or more, the mice were medicated as described below.

Ovaries on both sides were extirpated from all mice under anesthesia, and the mice were divided into 7 groups (Groups 1 to 7) at 5 mice/group. No drug was administered to Group 1. 5 µg/10 g body weight of 17β-estradiol suspended in physiological saline was daily intraperitoneally administered to Groups 2 to 7. Groups 3 to 7 were daily orally treated with the test drugs dissolved or suspended in 0.5% carboxymethylcellulose solution, while Group 2 was used as a control group by administering only the solvent. Dienogest was administered at a daily dose of from 0.01 to 10 mg/kg body weight, and medroxyprogesterone was administered at a daily dose of 100 mg/kg body weight.

After 4 weeks of medication, the cancer volume was measured to calculate the growth inhibition rate of the test drugs for the uterine cancer cells by the following equation:

$$\text{Growth inhibition (\%)} = \frac{\text{Average cancer volume of Group 2} - \text{Average cancer volume of the medicated group}}{\text{Average cancer volume of Group 2} - \text{Average cancer volume of Group 1}} \times 100$$

The results are shown in Table 1.

TABLE 1

Growth inhibition for a cell line from human uterine cancer (Ishikawa cell line)

| Group No. | Type of the drug tested | Dose, mg/kg/day | Cancer volume, mm³ | Growth inhibition, % |
|---|---|---|---|---|
| 1 | (No medication) | — | 559 | — |
| 2 to 7 | (Estrogen administered) | | | |
| | Control | — | 1733 | 0 |
| | Dienogest | 0.01 | 750 | 84 |
| | Dienogest | 0.1 | 421 | 112 |
| | Dienogest | 1 | 461 | 108 |
| | Dienogest | 10 | 507 | 104 |
| | Medroxyprogesterone | 100 | 916 | 70 |

Note: The FIGS. in the table represent an average of measurements for individuals in the group (n = 5).

As demonstrated in the results of Table 1, in the groups where dienogest was used at a daily dose of 0.1 mg/kg or higher, growth of the uterine cancer cells was completely inhibited, while medroxyprogesterone at a daily dose of as high as 100 mg/kg exhibited a growth inhibition of only 70%. Dienogest exhibited a therapeutic effect stronger than that of medroxyprogesterone even at a dose as low as approximately 1/10,000 to 1/1,000 of the medroxyprogesterone.

Experiment 2: Growth Inhibitory Action for a Cell Line from Human Well-Differentiated Uterine Cancer (Hec88-nu Cell Line)

CB-17 SCID female mice having a body weight of from 19 to 28 g, and Hec88-nu cell line (Morisawa et al., Nihon Rinsho Saibo Gakkai Zasshi (J. Jpn. Soc. Clin. Cytol.), 26, 3, 433–442, 1987), which is a cell line from human well-differentiated uterine cancer, were used. It is known that the growth of Hec88-nu cell line is not inhibited by medroxyprogesterone (Kato et alo, Hum. Cell, 4, 2, 165–170, 1991).

By repeating the procedure of Experiment 1, the cell line culture was subcutaneously implanted in the back of one mouse, and after its growth and extirpation, 40 mg/mouse of the extirpated cancer was subcutaneously implanted in the back of other 35 mice. When the implanted cancer had grown to a volume of 75 mm³ or more, the mice were medicated as described below.

Ovaries on both sides were extirpated from all mice under anesthesia, and the mice were divided into 8 groups (Groups 1 to 8) at 4 to 5 mice/group. No drug was administered to Group 1. 5 µg/10 g body weight of 17β-estradiol suspended in physiological saline was daily intraperitoneally administered to Groups 2 to 8. Groups 3 to 8 were daily orally administered with the test drugs dissolved or suspended in 0.5% carboxymethylcellulose solution, while Group 2 was used as a control group by administering only the solvent by repeating the procedure of Experiment 1.

After 4 weeks of medication, the cancer volume was measured to calculate the growth inhibition rate of the test drug for the uterine cancer cells as in the case of Experiment 1. The results are shown in Table 2.

TABLE 2

Growth inhibition for a cell line from human uterine cancer (Hec88-nu cell line)

| Group No. | Type of the drug tested | Dose, mg/kg/day | Cancer volume, mm³ | Growth inhibition, % |
|---|---|---|---|---|
| 1 | (No medication) | — | 595 | — |
| 2 to 8 | (Estrogen administered) | | | |
| | Control | — | 1728 | 0 |
| | Dienogest | 0.01 | 1080 | 57 |
| | Dienogest | 0.1 | 760 | 85 |
| | Dienogest | 1 | 756 | 86 |
| | Medroxyprogesterone | 100 | 1845 | −10 |
| | Tamoxifen | 1 | 1741 | 1 |
| | Tamoxifen | 10 | 1523 | 18 |

Note: The FIGS. in the table represent an average of measurements for individuals in the group (n = 4 or 5).

As demonstrated in the results of Table 2, dienogest at a daily dose of so low as 0.01 mg/kg exhibited a growth inhibition of the uterine cancer cells of more than 50%, while medroxyprogesterone at a daily dose of as high as 100 mg/kg failed to show any growth inhibition. Tamoxifen also failed inhibit the growth of the uterine cancer cells even when the dose was increased to 10 mg/kg.

It was then estimated that the carcinostatic of the present invention should have a cancer growth inhibitory mechanism different from that of the conventional progestin or antiestrogen, and would be effective for the types of cancers that failed to sufficiently respond to the conventional hormonotherapies.

Experiment 3: Growth Inhibitory Action for a Cell Line from Human Breast Cancer (MCF-7)

CB-17 SCID female mice having a body weight of from 17 to 25 g, and MCF-7 (Soule et al., J. Natl. Cancer Inst., 51, 1409–1413, 1973), which is a cell line from human breast cancer, were used.

By repeating the procedure of Experiment 1, the cell line culture was subcutaneously implanted in the back of one mouse, and after its growth and extirpation, 80 mg/mouse of the extirpated cancer was subcutaneously implanted in the back of other 30 mice on their left side. 0.5 mg/kg/day of 17β-estradiol suspended in physiological saline was daily intraperitoneally administered to each mouse, and when the implanted cancer had grown to a volume of 100 mm³ or more, the mice were medicated as described below.

Ovaries on both sides were extirpated from all mice under anesthesia, and the mice were divided into 6 groups (Groups 1 to 6) at 5 mice/group. No drug was administered to Group 1. 5 µg/10 g body weight of 17β-estradiol suspended in physiological saline was daily intraperitoneally administered to Groups 2 to 6. Groups 3 to 6 were daily orally administered with the test drugs dissolved or suspended in 0.5% carboxymethylcellulose solution, while Group 2 was used as a control group by administering only the solvent. Dienogest was used at a daily dose of from 0.01 mg/kg to 0.1 mg/kg, medroxyprogesterone was used at a daily dose of 100 mg/kg, and tamoxifen was used at a daily dose of 10 mg/kg.

After 4 weeks of medication, the cancer volume was measured to calculate the growth inhibition rate of the test drug for the breast cancer cells as in the case of Experiment 1. The results are shown in Table 3.

TABLE 3

Growth inhibition for a cell line from human breast cancer (MCF-7)

| Group No. | Type of the drug tested | Dose, mg/kg/day | Cancer volume, mm³ | Growth inhibition, % |
| --- | --- | --- | --- | --- |
| 1 | (No medication) | — | 88 | — |
| 2 to 6 | (Estrogen administered) | | | |
| | Control | — | 462 | 0 |
| | Dienogest | 0.01 | 87 | 100 |
| | Dienogest | 0.1 | 79 | 102 |
| | Medroxyprogesterone | 100 | 231 | 62 |
| | Tamoxifen | 10 | 205 | 69 |

Note: The FIGS. in the table represent an average of measurements for individuals in the group (n = 5).

As evident in the results of Table 3, medroxyprogesterone at a daily dose of 100 mg/kg or tamoxifen at a daily dose of 10 mg/kg failed to sufficiently inhibit the growth of the breast cancer cells. In contrast, dienogest could substantially inhibit the growth at a dose as low as approximately 1/10,000 to 1/1,000 of the medroxyprogesterone and approximately 1/1,000 to 1/100 of the tamoxifen.

Accordingly, dienogest is expected to have therapeutic effects significantly higher than those of the conventional drugs not only for the uterine cancer but also for the breast cancer and the like.

Experiment 4: Confirmation of the Presence or Absence of the Corticoid Action of Dienogest Wistar male rats with a body weight of from 170 to 210 g were used in groups of 6 rats/group.

Adrenal glands on both sides were extirpated from the rats under anesthesia.

First series of the test drugs were dienogest prepared by repeating the procedure of Experiment 1 and dexamethasone dissolved in sesame oil. The dienogest at an oral dose of from 10 to 100 mg/kg and dexamethasone at a subcutaneous dose of 0.1 mg/kg were administered, while only the solvent of the same volume was administered to the control group.

Second series of test drugs were dexamethasone dissolved in sesame oil and aldosterone dissolved in sesame oil, which were respectively subcutaneously administered to different groups of the rats at a dose of 0.1 mg/kg for dexamethasone and at a dose of 0.025 mg/kg for aldosterone, while only the solvent of the same volume was administered to the control group. Just after the administration of the test drugs, 30 ml/kg of physiological saline was intraperitoneally administered, and urine was collected for 4 hours to measure the urine volume and electrolyte concentration of the urine.

The urine volume and the ratio of sodium ion to potassium ion excreted in the urine (Na/K ratio) were used as indexes of the corticoid action.

The results are shown in Table 4.

TABLE 4

| | Corticoid action | | | | |
| --- | --- | --- | --- | --- | --- |
| | Dose | Urine volume | | Urinary Na/K ratio | |
| Group | mg/kg | ml | P | | P |
| Control | — | 2.4 | | 0.78 | |
| Dienogest | 10 | 2.4 | N.S. | 0.67 | N.S. |
| Dienogest | 30 | 2.5 | N.S. | 0.91 | N.S. |
| Dienogest | 100 | 2.7 | N.S. | 0.85 | N.S. |

TABLE 4-continued

| | Corticoid action | | | | |
| --- | --- | --- | --- | --- | --- |
| | Dose | Urine volume | | Urinary Na/K ratio | |
| Group | mg/kg | ml | P | | P |
| Dexamethasone | 0.1 | 4.7 | <0.01 | 0.45 | <0.01 |
| Control | — | 2.4 | | 0.86 | |
| Dexamethasone | 0.1 | 4.5 | <0.01 | 0.41 | <0.01 |
| Aldosterone | 0.025 | 1.5 | <0.05 | 0.12 | <0.01 |

Note: The FIGS. in the table represent an average of measurements for individuals in the group (n = 6).
P: The result of the analysis for the difference in the average of measurements between the control group and the medicated group by Dunnet multiple comparison method.
N.S.: not significant.

As evident in the results shown in Table 4, the dienogest-medicated rat groups failed to exhibit any significant difference from the control group in neither the urine volume nor the urinary Na/K ratio even when the dose was as high as 100 mg/kg, and neither the glucocorticoid activity as typically exhibited by dexamethasone nor the mineralocorticoid activity as typically exhibited by aldosterone was recognized in the dienogest-medicated rat groups.

Experiment 5: Comparison of the Androgen Action Between Dienogest and the Conventional Drug Wistar-Imamichi male rats with a body weight of from 40 to 60 g were used in groups of 5 to 6 rats/group.

Testes were extirpated from the rats under anesthesia. The test drugs were prepared by repeating the procedure of Experiment 1, and dienogest at a dose of from 10 to 100 mg/kg and medroxyprogesterone at a dose of from 30 to 300 mg/kg were orally administered, while only the solvent of the same volume was administered to the control groups.

After daily administration for seven days, ventral prostate was extirpated to measure its weight. The percentage of the average prostate weight of the medicated group in relation to the average prostate weight of the control group was used for the index of the androgenic action. The results are shown in Table 5.

TABLE 5

| | Androgenic action | | |
| --- | --- | --- | --- |
| | Dose | Weight of prostate | |
| Group | mg/kg/day | mg | % |
| Control | — | 5.8 | 100 |
| Dienogest | 10 | 6.2 | 107 |
| Dienogest | 30 | 6.5 | 112 |
| Dienogest | 100 | 6.6 | 114 |
| Control | — | 6.8 | 100 |
| Medroxyprogesterone | 30 | 9.2 | 135 |
| Medroxyprogesterone | 100 | 10.3 | 151 |
| Medroxyprogesterone | 300 | 13.5 | 199 |

Note: The FIGS. in the table represent an average of measurements for individuals in the group (n = 5 or 6).

As demonstrated in the results shown in Table 5, dienogest did not show any significant androgenic action even when it was administered at a dose of as high as 100 mg/kg, while medication of medroxyprogesterone at a dose of 100 mg/kg or more resulted in an increase of more than 50% in the prostate weight, indicating a significant androgenic action of the drug.

In view of such results, it was estimated that dienogest is far less likely to be accompanied by side effects induced by the androgenic action compared to the medroxyprogesterone.

In Schubert et al., Elsevier Science Publishers ed., Natural Products Chemistry, 1984, 143–158, supra, there is reported that dienogest only has a slight anti-estrogenic activity. When such disclosure is taken into consideration with the results of Experiment 2 or 3, it would be understood that the therapeutic effects of the carcinostatic of the present invention could not simply be explained in terms of such anti-estrogenic activity.

As demonstrated in the experimental results as described above, dienogest exhibits excellent inhibitory effect in experimental models wherein the conventional progestin or the antiestrogen failed to show the effect even when dienogest is used at a dose significantly lower than such conventional drugs. It was then estimated that the carcinostatic of the present invention has a mechanism quite different from that of the conventional progestins or antiestrogens, and would be effective for the sex hormone-dependent cancers which were not responsive to conventional hormonotherapies.

Furthermore, the carcinostatic of the present invention is substantially free from the androgenic action or the corticoid action, and therefore, it is expected to be a safe drug free from side effects including thrombosis, cardiocoronary diseases, arteriosclerosis, Cushing's syndrome, moon face, and the like.

The carcinostatic of the present invention is also expected to be free from other unknown side effects since the dose of the dienogest required for inhibiting the growth of the sex hormone-dependent cancers is comparable to the dose of the dienogest as an oral contraceptive approved in Germany, namely, a daily dose of 2 mg, and its safety at a daily dose of 2 mg has also been confirmed in its clinical experiments as a therapeutic agent for endometriosis.

Next, dosage form of the carcinostatic of the present invention is described. The carcinostatic of the present invention may be administered either alone or with other drugs. Exemplary oral and non-oral dosage forms include, tablets, capsules, sugar- or film-coated tablets, granules, fine granules, powders, liquid solutions or suspensions, emulsions, lipid emulsions, and ointments. It may be also administered as rectal or vaginal suppositories, or intramuscular or intravenous injections. It may also be produced into sustained-release preparations in the form of plaster tapes, patches, or subcutaneous implants and the like.

The carcinostatic of the present invention may typically be administered at one to five times a day at a daily dose of from about 0.05 to 100 mg, and preferably, from 0.5 to 10 mg in the case of an adult. The dose, however, may vary in accordance with the age, body weight, and health conditions of the patient as well as the way of dosage.

The carcinostatic of the present invention may be used in various conventional forms of hormonotherapy. It may be used alone or in combination with a known hormonotherapeutic carcinostatic in hormonotherapy of the sex hormone-dependent cancers; in combination with a chemotherapeutic agent in a so called hormonochemotherapy; or as an adjuvant hormonotherapy in combination with a surgical therapy, for a prophylactic or therapeutic purpose, or for the purpose of preventing the recurrence of the cancer.

The present invention is further described by referring to the following Examples which by no means limit the scope of the invention.

EXAMPLE 1

| Dienogest | 0.5 g |
| Lactose | 92.5 g |
| Corn starch | 49.0 g |
| Talc | 3.0 g |
| Magnesium stearate | 5.0 g |

The ingredients were adequately mixed, and the mixture was subjected to wet granule compaction to produce 150 mg tablets each containing 0.50 mg of the dienogest.

EXAMPLE 2

| Dienogest | 2.0 g |
| Lactose | 87.0 g |
| Corn starch | 6.0 g |
| Magnesium stearate | 5.0 g |

The ingredients were mixed, and the mixture was filled in Japanese Pharmacopoeia #3 capsules.

EXAMPLE 3

| Dienogest | 1.0 g |
| Polysorbate 80 | 1.0 g |
| Witepsol (S-55) | 98.0 g |

The ingredients were kneaded at an elevated temperature, and filled in a plastic package to produce suppositories each weighing 1.0 g.

EXAMPLE 4

| Dienogest | 1.0 g |
| Polyoxyethylene lauryl ether | 39.0 g |
| Glycerin | 20.0 g |

The ingredients were adequately melt kneaded at an elevated temperature, and filled in a package to produce suppositories each weighing 1.0 g.

EFFECTS OF THE INVENTION

The carcinostatic of the present invention is expected to exert therapeutic effects comparable or superior to the conventional hormonotherapeutic agents at a dose far lower than the dose of such conventional hormonotherapeutic agents in the therapy of sex hormone-dependent cancers such as uterine cancer and breast cancer. Accordingly, the carcinostatic of the present invention is utterly free from side effects that the conventional high-dose hormonotherapy had suffered. Furthermore, the carcinostatic of the present invention is expected to exert its effects for a broad range of cancer cases including the cases that had failed to respond to the conventional hormonotherapies since the carcinostatic of the present invention is estimated to act in a mechanism different from the conventional progestins or the antiestrogens.

We claim:

1. A method of treatment and/or prevention of the recurrence of sex hormone-dependent cancer, comprising administering to a patient in need thereof a pharmaceutical composition containing an effective amount of at least dienogest or a solvate thereof as an effective component and a pharmacologically acceptable carrier.

2. A method of claim 1, wherein said effective amount is a daily dose from 0.05–100 mg.

3. A method of claim 1, wherein said effective amount is a daily dose from 0.5–10 mg.

4. A method of claim 1, wherein said composition is administered via a route selected from the group consisting of oral, suppositories, topical, intramuscular, intravenous, plaster tapes, patches and subcutaneous implants.

5. A method of claim 4, wherein said route is oral.

6. A method of claim 1, wherein said method is a method for treatment.

7. A method of claim 1, wherein said method is a method for the prevention of the recurrence.

8. A method of claim 1, wherein said cancer is selected from the group consisting of uterine cancer, breast cancer, prostate cancer and thyroid gland cancer.

9. A method of treatment and/or prevention of the recurrence of uterine cancer or breast cancer, comprising administering to a patient in need thereof a pharmaceutical composition containing an effective amount of at least dienogest or a solvate thereof as an effective component and a pharmacologically acceptable carrier.

10. A method of claim 9, wherein said effective amount is a daily dose from 0.05–100 mg.

11. A method of claim 9, wherein said effective amount is a daily dose from 0.5–10 mg.

12. A method of claim 9, wherein said composition is administered via a route selected from the group consisting of oral, suppositories, topical, intramuscular, intravenous, plaster tapes, patches and subcutaneous implants.

13. A method of claim 12, wherein said route is oral.

14. A method of claim 9, wherein said method is a method for treatment.

15. A method of claim 9, wherein said method is a method for the prevention of the recurrence.

16. A method of claim 9, wherein said cancer is breast cancer.

17. A method of claim 9, wherein said cancer is uterine cancer.

18. A method of treatment and/or prevention of the recurrence of hormone-dependent cancer, comprising administering to a patient in need thereof a pharmaceutical composition containing a therapeutically effective amount of at least dienogest or a solvate thereof as an effective component and a pharmacologically acceptable carrier.

19. A method of claim 18, wherein said effective amount is a daily dose from 0.05–100 mg.

20. A method of claim 18, wherein said effective amount is a daily dose from 0.5–10 mg.

21. A method of claim 18, wherein said composition is administered via a route selected from the group consisting of oral, suppositories, topical, intramuscular, intravenous, plaster tapes, patches and subcutaneous implants.

22. A method of claim 21, wherein said route is oral.

23. A method of claim 18, wherein said method is a method for treatment.

24. A method of claim 18, wherein said method is a method for the prevention of the recurrence.

* * * * *